(12) United States Patent
Ali

(10) Patent No.: US 9,707,243 B2
(45) Date of Patent: Jul. 18, 2017

(54) TOPICAL COMPOSITION WITH VITAMIN D3

(71) Applicants: Sadat A. Ali, Carol Stream, IL (US); Haifa Abdulaziz Alturki, Alkhobar (SA)

(72) Inventor: Sadat M. Ali, Carol Stream, IL (US)

( * ) Notice: Subject to any disclaimer, the term of this patent is extended or adjusted under 35 U.S.C. 154(b) by 0 days.

(21) Appl. No.: 15/125,141

(22) PCT Filed: Mar. 10, 2014

(86) PCT No.: PCT/US2014/022699
§ 371 (c)(1),
(2) Date: Sep. 9, 2016

(87) PCT Pub. No.: WO2015/137912
PCT Pub. Date: Sep. 17, 2015

(65) Prior Publication Data
US 2016/0375040 A1    Dec. 29, 2016

(51) Int. Cl.
| | | |
|---|---|---|
| *A61K 31/59* | (2006.01) | |
| *A61K 31/593* | (2006.01) | |
| *A61K 36/752* | (2006.01) | |
| *A61K 36/886* | (2006.01) | |
| *A61K 9/00* | (2006.01) | |
| *A61K 9/06* | (2006.01) | |
| *A61K 47/46* | (2006.01) | |
| *A61K 36/53* | (2006.01) | |
| *A61K 47/10* | (2017.01) | |

(52) U.S. Cl.
CPC .......... *A61K 31/593* (2013.01); *A61K 9/0014* (2013.01); *A61K 9/06* (2013.01); *A61K 36/53* (2013.01); *A61K 36/752* (2013.01); *A61K 36/886* (2013.01); *A61K 47/10* (2013.01); *A61K 47/46* (2013.01)

(58) Field of Classification Search
CPC .................................................. A61K 31/593

USPC ......................................................... 514/167
See application file for complete search history.

(56) References Cited

U.S. PATENT DOCUMENTS

| | | |
|---|---|---|
| 5,380,720 A | 1/1995 | Deluca et al. |
| 5,597,575 A | 1/1997 | Breitbarth |
| 7,262,224 B2 | 8/2007 | Chong |
| 2004/0091551 A1 | 5/2004 | Damji |
| 2006/0034779 A1 | 2/2006 | Arkin et al. |
| 2007/0248555 A1 | 10/2007 | Watson |
| 2010/0055161 A1 | 3/2010 | Ahn |
| 2010/0093678 A1 | 4/2010 | Della-Fera et al. |
| 2010/0215726 A1 | 8/2010 | Roth |
| 2011/0207697 A1 | 8/2011 | Ono et al. |
| 2011/0229536 A1 | 9/2011 | Kvitnitsky et al. |
| 2011/0319805 A1 | 12/2011 | Morris |
| 2013/0319889 A1 | 12/2013 | DeSantis |

OTHER PUBLICATIONS

"Vitamin D3 Cream", King Supplements, 3 pages printed from d3cream.kingsupplements.com/?gclid=COWUgeCJboCFVTNOgodwiwAJg on Nov. 17, 2013.

*Primary Examiner* — Raymond Henley, III
(74) *Attorney, Agent, or Firm* — Richard C. Litman

(57) ABSTRACT

The topical composition with Vitamin D3 includes Vitamin D3, one or more aromatic oils, and aloe vera gel. Vitamin D3 is soluble in aromatic oils, and aloe vera gel enables transport through the stratum corneum so that the composition may be used for fulfilling daily requirements, treatment of bone conditions, such as rickets and osteomalacia, and supportive therapy in osteopenia and osteoporosis. The aromatic oil may be a citric acid extract (e.g., orange oil extracted from orange peels), lavender oil, or any other aromatic oil in which Vitamin D3 is soluble. Optionally, the composition may include excipients, such as a permeability enhancer (e.g., glycerine and water), a preservative (e.g., a carbomer, methyl paraben, EDTA, or the like), or other additives that do not affect the active ingredients. The composition is preferably formulated as a cream or emulsion.

11 Claims, 2 Drawing Sheets

TOPICAL COMPOSITION WITH VITAMIN D3

TECHNICAL FIELD

The present invention relates to Vitamin D supplements, and particularly to a topical composition with Vitamin D3 formulated for transdermal delivery to a patient in need thereof, e.g., patients with rickets, osteomalacia, osteopenia, and osteoporosis.

BACKGROUND ART

There are two principle types of Vitamin D, Vitamin D2 and D3. Vitamin D2 (ergocalciferol) is derived from such sources as fortified milk, herring, mackerel, tuna, salmon, sardines, eggs, fortified cereals, and baked goods, while Vitamin D3 (cholecalciferol) is a pro-hormone and an essential nutrient produced in the skin with exposure to UV rays, consumption of animal products and fortified foods. Vitamin D3 can be produced photochemically by the action of sunlight or ultraviolet light from the precursor sterol 7-dehydrocholesterol, which is present in the epidermis or skin. Vitamin D3 can also be consumed in the form of fish oil or foods, such as eggs or fish. Analogs of Vitamin D may be produced synthetically.

Vitamin D2 and D3 are subsequently 25-hydroxylated in the liver to form 25-hydroxyvitamin D2 (25OHD2) and 25-hydroxyvitamin D3 (25OHD3), respectively. 25OHD2 and 25OHD3 represent the main body reservoir and transport form of vitamin D and are stored in adipose tissue or are tightly bound by a transport protein while in circulation.

The exact levels of 25OHD2 and 25OHD3 that reflect optimal body stores are uncertain. Mild to modest deficiency can be associated with osteoporosis or secondary hyperparathyroidism. Severe deficiency may lead to failure to mineralize newly formed osteoid in bone, resulting in rickets in children and osteomalacia in adults.

Deficiency of Vitamin D is generally due to inadequate exposure to the sun or due to its low content in the diet. As early as the 1980's, it was found that the ethnic Saudi population has low Vitamin D. Extensive studies have shown that deficiency exists not only in the winter, but also in the summer months due to non-exposure to the sun. It has been found in the healthy Saudi population that Vitamin D deficiency exists in about 40-60% of men and women over 50 years of age. Recent studies put the deficiency of Vitamin D at 95-100%.

For any drug, large proportions of oral prescriptions are never taken at all. Recent estimates for noncompliance range from study to study, with ranges of 62 to 84 percent using electronic monitoring. In other words, many do not comply with the recommended dosages of oral prescriptions.

Conventional routes of administration of Vitamin D include oral or injectable administration. For oral Vitamin D and calcium supplementation, the compliance is reported between 20-60%. It has been reported that at the end of 3 months, only 23.8% of patients were taking the supplementation and another 26.2% were partially compliant. Physicians attempted to address this problem by prescribing monthly, quarterly and yearly dosages. A yearly oral dose of 500,000 international units was found to result in an increased risk of falls and fractures. Recently, quarterly dosages of 150,000 IU of Vitamin D and intermittent large doses of vitamin D have been found to be ineffective.

Deficiency of Vitamin D is often significant in those who are non-compliant, i.e., fail to take prescribed dosages of oral Vitamin D. Typically, non-compliance is associated with patients who are already required to take a number of other oral medications. It was reported that between 40-45% of patients become non-compliant within six months of initiating therapy for osteopenia and osteoporosis. It was found that about 12% of elderly U.S. patients take ≥12 medications and 23% take at least 5 prescription medications. Requiring additional oral medications becomes burdensome for such patients. As Vitamin D is an essential part of osteopenia and osteoporosis treatment, a suitable alternative is desirable. An alternative to oral supplementation would likely increase compliance of patients already burdened with other oral medications.

Thus, a topical composition with vitamin D3 solving the aforementioned problems is desired.

DISCLOSURE OF INVENTION

The topical composition with Vitamin D3 includes Vitamin D3, one or more aromatic oils, and aloe vera gel. Vitamin D3 is soluble in aromatic oils, and aloe vera gel enables transport through the stratum corneum so that the composition may be used for treatment of bone conditions, such as rickets, osteomalacia, osteopenia, and osteoporosis. The aromatic oil may be a citric acid extract (e.g., orange oil extracted from orange peels), lavender oil, or any other aromatic oil in which Vitamin D3 is soluble. Optionally, the composition may include excipients, such as a permeability enhancer (e.g., glycerine and water), a preservative (e.g., a carbomer, methyl paraben, EDTA, or the like), or other additives that do not affect the active ingredients. The composition is preferably formulated as a cream or emulsion.

The topical composition with Vitamin D3 may be applied topically to deliver Vitamin D3 to a human subject. Vitamin D3 may cross the skin bather and pass into the body's systemic circulation once the topical composition with Vitamin D3 is applied to the skin.

These and other features of the present invention will become readily apparent upon further review of the following specification and drawings.

BRIEF DESCRIPTION OF THE DRAWINGS

Similar reference characters denote corresponding features consistently throughout the attached drawings.

BEST MODE FOR CARRYING OUT THE INVENTION

Figure 1:
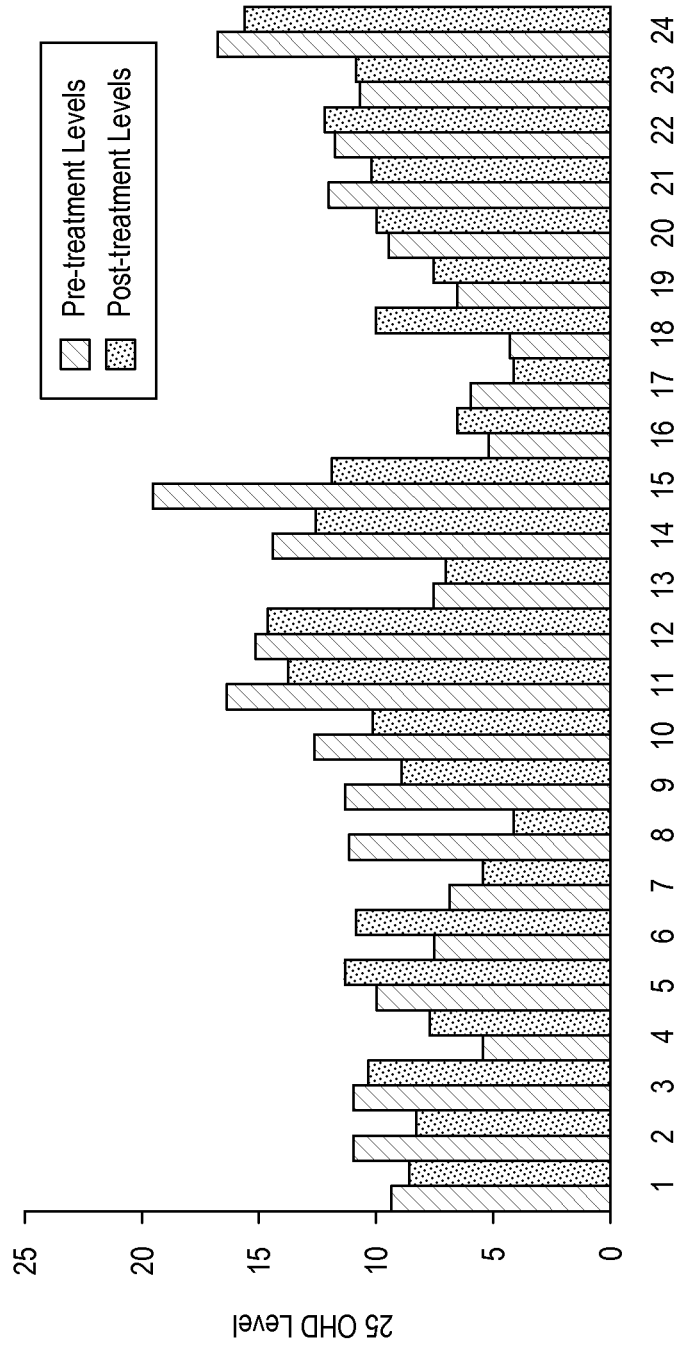
FIG. 1 is a graph showing pre- and post-treatment 25OHD levels of participants in the control group undergoing testing of a topical composition with Vitamin D3 according to the present invention.

The topical composition with Vitamin D3 includes Vitamin D3, one or more aromatic oils, and aloe vera gel. Vitamin D3 is soluble in aromatic oils, and aloe vera gel enables transport through the stratum corneum so that the composition may be used for treatment of bone conditions, such as rickets, osteomalacia, osteopenia, and osteoporosis. The aromatic oil may be a citric acid extract (e.g., orange oil extracted from orange peels), lavender oil, or any other aromatic oil in which Vitamin D3 is soluble. Optionally, the composition may include excipients, such as a permeability enhancer (e.g., glycerine and water), a preservative (e.g., a carbomer, methyl paraben, EDTA, or the like), or other additives that do not affect the active ingredients. The composition is preferably formulated as a cream or emulsion.

The topical composition with Vitamin D3 may be applied topically to deliver Vitamin D3 to a human subject. Vitamin D3 may cross the skin barrier and pass into the body's systemic circulation once the topical composition with Vitamin D3 is applied to the skin.

The skin is composed of two primary layers, the epidermis on the outside and the dermis on the inside. The stratum corneum is the outermost layer of the epidermis, consisting of dead cells. The stratum corneum forms a barrier to protect underlying tissue from infection, dehydration, chemicals and mechanical stress. Although the stratum corneum is an efficient barrier, the topical composition with Vitamin D3 is able to penetrate the stratum corneum and reach the underlying tissues and blood vessels. Accordingly, the topical composition with Vitamin D3 may provide a suitable alternative to oral Vitamin D supplements.

The term composition, as used herein, may refer to a combination of ingredients to form a lotion, gel, cream, ointment, paste, foam, aerosol spray, and the like. Topical, as used herein, may refer to application of a substance to a specific area of the skin.

The topical composition with Vitamin D3 includes aloe vera gel. Aloe vera is a succulent plant species. The long, green leaves of the aloe vera plant contain aloe vera gel. Aloe vera gel is typically used for manufacture of topical-like ointments and gel preparations. It has been found that aloe vera gel has the ability to improve the bioavailability of co-administered vitamins in human subjects. Aloe vera gel may also enhance skin penetration of the topical composition with Vitamin D3. The topical composition with Vitamin D3 may include one or more other plant extracts from succulent plants to enhance skin penetration, including, but not limited to, cacti and seaweed extract.

The topical composition with Vitamin D3 may include one or more aromatic oils. Vitamin D is a fat soluble vitamin that dissolves easily in aromatic oils. Suitable aromatic oils may include orange oil (*Citrus Sinensis*) and/or Lavender oil (*Lavandula officinalis*). Other suitable aromatic oils that may be included in the composition include one or more of vanilla oil, sandalwood oil, cedar wood oil, mandarin orange oil, cinnamon oil, lemongrass oil, rosehip oil, and peppermint oil.

The topical composition with Vitamin D3 may include one or more suitable preservatives. Suitable preservatives may include, for example, EDTA, Carbomer, and methyl paraben.

The topical composition with Vitamin D3 may include glycerine. Glycerine is a humectant, i.e., it absorbs ambient water. Glycerine may also enhance penetration of the topical composition with Vitamin D3.

The topical composition with Vitamin D3 may include water. Water may be used to enhance penetration of the composition in the skin. Hydration of the stratum corneum may increase the penetration of both hydrophilic and hydrophobic drugs. Water suitable for the present composition may be potable water. The water may be deionized, filtered, distilled, or tap water from the spigot.

The topical composition with Vitamin D3 may include about 5% Vitamin D3, about 5% aromatic oils, about 10% glycerine, about 10% preservative(s), and about 70% aloe vera. In an exemplary embodiment, the topical composition with Vitamin D3 may include about 5 grams Vitamin D3, about 5 ml aromatic oils, about 10 ml of glycerine, about 10 ml of preservatives, and about 70 ml of aloe vera.

The topical composition with Vitamin D3 may be made by dissolving an amorphous powder of Vitamin D3 to form a paste. Vitamin D is fat soluble and lipophilic. Suitable aromatic oils may be added to the paste. For example, orange oil (*Citrus Sinensis*) and/or Lavender oil (*Lavandula officinalis*) may be added. Preferably, the orange oil is organic and 100% pure, i.e., extracted from fresh orange peel. Preferably, the lavender oil is organic and 100% pure, i.e., extracted from Lavender flowers. The paste may then be mixed with 100% aloe vera gel to form a homogeneous gel. The paste may be mixed in a small speed ultracentrifuge in order to uniformly disperse the Vitamin D throughout the gel. During the process of mixing, other inactive ingredients may be added. Suitable inactive ingredients that may be added include preservatives, such as carbomer 940, Methyl Paraben, and Triethylamine.

The composition may deliver 5000 IU of Vitamin D3 in 1 ml (gram) of gel. Daily application of the topical composition with Vitamin D3 to the skin was found to return the 25OHD level to a minimum normal level of 30 ng/mL within a 90-day period. Accordingly, Vitamin D3 may safely be delivered through the dermal route.

As discussed above, topical administration of the topical composition with Vitamin D3 may allow Vitamin D3 to pass into the body's systemic circulation. As such, the topical composition with Vitamin D3 may be useful for treating bone diseases for which Vitamin D supplementation is essential, such as osteopenia, osteoporosis, rickets, and osteomalacia.

Transdermal administration of Vitamin D3, as described herein, may be particularly desirable for the elderly, for children who require vitamin D supplementation, and in patients requiring Vitamin D3 supplementation who already have a large medication burden.

The following example is illustrative only, and is not intended to limit the present teachings.

EXAMPLE

A study was carried out on 50 women with low vitamin D. The women were healthy and unmarried. Age, weight, height, and detailed medical history were recorded. Meticulous clinical examination was performed to rule out any diseases. A complete blood picture, including serum calcium, phosphorous, alkaline phosphatase, Parathormone and 25 Hydroxy-vitamin D (25OHD), was obtained. Two women had >30 ng/mL of 25OHD and were excluded from the study. The 25-Hydroxy Vitamin D3 level was measured in house by chemiluminescence immunoassay (CLIA), and 30 ng/mL was taken as normal, 21-29 ng/mL as insufficiency and 20 ng/mL as deficiency.

The participants were divided into two groups of 24 women each. All participants unequivocally agreed not to change their dietary habits and life style until the study was over. The group of women participating in the study were asked to apply the topical composition with Vitamin D3. Each gram of the composition delivered 5000 IU of vitamin D3. The second group used 1 gram of aloe vera gel. The participants had no knowledge to which group they belong. A second blood sample was taken at the end of 3 months, and the data was entered in the database and analyzed using a t-test to compare means between the two groups for all the parameters tested before and after topical use of VD and AVG. All tests were performed using SPSS (Statistical Package for the Social Sciences), version 14.0, Chicago, Ill.

A p value of <0.05 was considered statistically significant with Confidence Interval (CI) of 95%.

Results: The data of the 48 women participating in the study follows. The mean age was 22.58±1.95 with Body Mass Index (BMI) of mean 19.95±3.15 kg/M2. The demographic data is shown in Table 1.

TABLE I

Demographic Data

| Age | 22.58 ± 1.95 (19-27) | Years |
|---|---|---|
| BMI: | 19.95 ± 3.15 (13.8-27.2) | Kg/M$^2$ |
| Hemoglobin Level: | 11.97 ± 0.97 (9.4-13.3) | g/dl |
| Calcium: | 9.97 ± 0.54 (8.2-10.5) | mg/dl |
| Phosphorus: | 3.74 ± 0.54 (2.9-4.8) | mg/dl |
| Alkaline Phosphatase: | 78.37 ± 26.61 (70-135) | IU |
| Parathormone: | 8.24 ± 3.9 (2.74-17) | pc/ml |
| 25OHD: | 11.22 ± 5.41 (4-28.9) | ng/mL |

Figure 2:
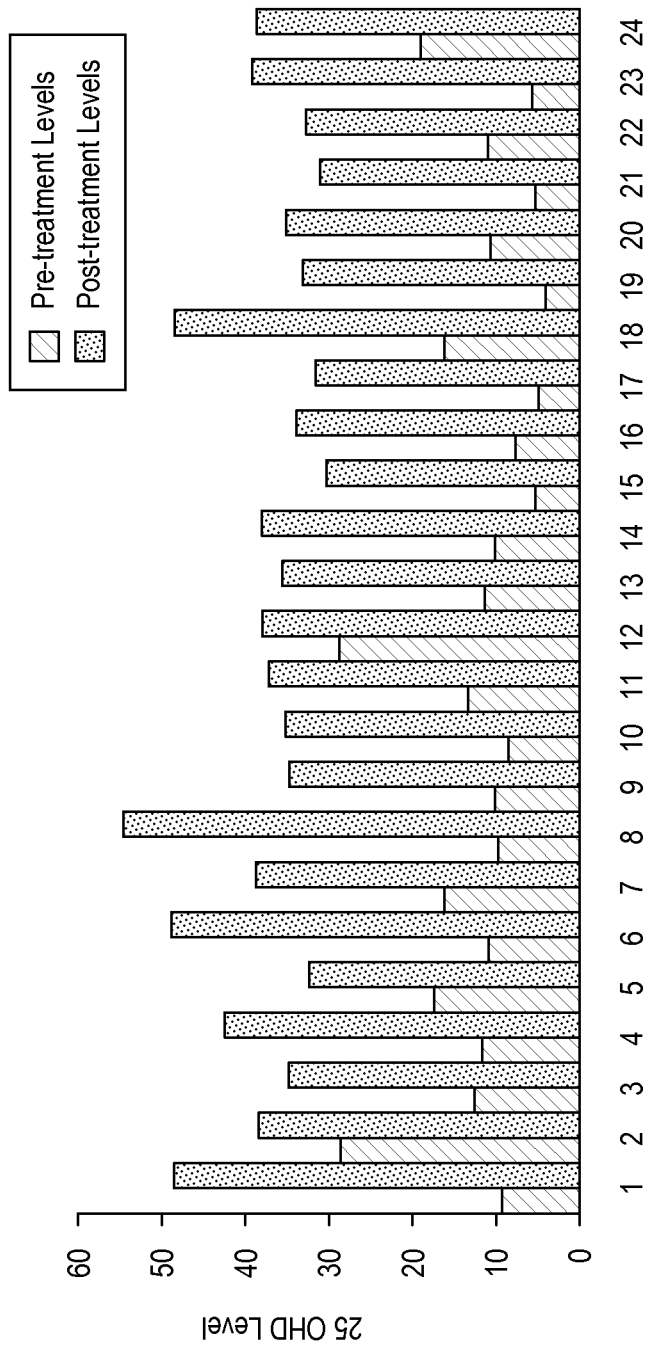
FIG. 2 is a graph showing pre- and post-treatment 25OHD levels of participants in the study group undergoing testing of a topical composition with Vitamin D3 according to the present invention.

FIG. 1 is a graph comparing pre and post treatment levels of 25OHD of participants in the control group. FIG. 2 is a graph comparing pre and post treatment levels of 25OHD of participants in the study group. In the control group there was no statistical change between the groups whereas in the study group, women who had lower levels of 25OHD showed marked improvement in the levels of 25OHD.

The average 25OHD level pretreatment was 11.54±5.41 ng/mL and post treatment was 23.77±15.17 ng/mL (P=CI 95%). In the study group the average BMI was 19.91±2.93 kg/M2 and control group was 20.0±3.41 kg/M2 (P value <0.2). The mean pre-treatment 25OHD was 12.05 ng/mL±6.54 and post-treatment was 37.95 ng/mL±6.43 (P=0.001 CI<28.582). In the control group the pre-treatment 25OHD was 11.4 ng/mL±3.97 and post-treatment was 10.58 ng/mL±3.03. In the control group the pre-treatment 25OHD was 10.4 ng/mL±3.97 and post-treatment was 9.58 ng/mL±3.03. The comparison between the two groups is shown in Table II.

TABLE II

| | Study Group | Control Group | P Value |
|---|---|---|---|
| Calcium | 9.0 ± 0.6 | 8.95 ± 0.48 | 0.6 |
| Phosphorus | 3.78 ± 0.66 | 3.7 ± 0.61 | 0.7 |
| Alkaline Phosphatase | 74.91 ± 24.84 | 82.25 ± 28.19 | 0.001 CI < −7.148 |
| Parathormone | 8.33 ± 4.13 | 9.15 ± 3.74 | 0.2 |
| 25 OHD pre-treatment | 12.05 ± 6.54 | 11.4 ± 3.97 | 0.4 |
| 25OHD Post-treatment | 37.95 ± 6.43 | 10.58 ± 3.03 | 0.001 CI < 28.5828 |

This randomized control study shows that Vitamin D3 can safely be delivered through the dermal route. This route could be important in the elderly and children who require vitamin D supplementation, and in patients who have a large medication burden.

It is to be understood that the present invention is not limited to the embodiments described above, but encompasses any and all embodiments within the scope of the following claims.

I claim:

1. A topical composition with Vitamin D3, comprising a mixture of:
    about 5% of Vitamin D3;
    about 5% of an aromatic oil;
    about 10% of glycerine;
    about 10% of a preservative; and
    about 70% of aloe vera gel.

2. The topical composition with Vitamin D3 according to claim 1, wherein said aromatic oil comprises orange oil (*Citrus Sinensis*).

3. The topical composition with Vitamin D3 according to claim 1, wherein said aromatic oil comprises Lavender oil (*Lavandula officinalis*).

4. The topical composition with Vitamin D3 according to claim 1, further comprising water.

5. The topical composition with Vitamin D3 according to claim 1, wherein the preservative is selected from the group consisting of carbomer 840, methyl paraben, and EDTA.

6. A topical composition with Vitamin D3, consisting essentially of:
    about 5% of Vitamin D3;
    about 5% of an aromatic oil;
    about 10% of glycerine;
    about 10% of a preservative; and
    about 70% of aloe vera gel.

7. The topical composition with Vitamin D3 according to claim 6, wherein the aromatic oil comprises orange oil (*Citrus Sinensis*).

8. The topical composition with Vitamin D3 according to claim 6, wherein the aromatic oil comprises Lavender oil (*Lavandula officinalis*).

9. The topical composition with Vitamin D3 according to claim 6, wherein the preservative selected from the group consisting of carbomer 840, methyl paraben, and EDTA.

10. A method of treating a patient having a condition characterized by Vitamin D deficiency, comprising the steps of:
    topically applying to the skin on a daily basis an effective amount of a composition having a mixture of:
        about 5% of Vitamin D3;
        about 5% of an aromatic oil;
        about 10% of glycerine;
        about 10% of a preservative;
        about 70% of aloe vera gel,
    wherein the effective amount includes 5000 IU per diem Vitamin D3;
    obtaining a blood sample of the patient;
    testing the blood sample for the level of 25-hydroxy Vitamin D; and
    repeating the testing during the daily application of the composition until the 25-hydroxy Vitamin D level is approximately 30 ng/mL.

11. The method of treating a condition according to claim 10, wherein the condition is osteopenia, osteoporosis, rickets, or osteomalacia.

* * * * *